(12) United States Patent
Rochat (10) Patent No.: US 8,974,416 B2
(45) Date of Patent: Mar. 10, 2015

(54) DISPOSABLE CASSETTE FOR AN INFUSION PUMP FOR MEDICAL USE AND METHOD FOR MANUFACTURE THEREOF

(76) Inventor: Jean-Denis Rochat, Genolier (CH)

( * ) Notice: Subject to any disclaimer, the term of this patent is extended or adjusted under 35 U.S.C. 154(b) by 0 days.

(21) Appl. No.: 13/518,474

(22) PCT Filed: Dec. 20, 2010

(86) PCT No.: PCT/CH2010/000317
§ 371 (c)(1),
(2), (4) Date: Aug. 23, 2012

(87) PCT Pub. No.: WO2011/075858
PCT Pub. Date: Jun. 30, 2011

(65) Prior Publication Data
US 2012/0310162 A1    Dec. 6, 2012

(30) Foreign Application Priority Data

Dec. 23, 2009  (CH) ..................... 1983/09

(51) Int. Cl.
*A61M 37/00* (2006.01)
*F04B 43/08* (2006.01)
*F04B 43/00* (2006.01)
*A61M 5/142* (2006.01)

(52) U.S. Cl.
CPC ..... *A61M 5/14224* (2013.01); *A61M 2205/128* (2013.01)
USPC ........... 604/153; 417/478; 417/479; 417/480; 251/331

(58) Field of Classification Search
USPC .......... 604/153; 417/63, 478–480; 251/9, 331
See application file for complete search history.

(56) References Cited

U.S. PATENT DOCUMENTS

| 4,304,260 | A | | 12/1981 | Turner | |
|---|---|---|---|---|---|
| 5,462,256 | A | * | 10/1995 | Minick et al. | 251/331 |
| 7,503,348 | B2 | * | 3/2009 | Irwin et al. | 137/625.68 |
| 2002/0159900 | A1 | * | 10/2002 | Lawless et al. | 417/478 |
| 2005/0260090 | A1 | * | 11/2005 | Stark et al. | 417/559 |

FOREIGN PATENT DOCUMENTS

| EP | 1400254 | 3/2004 |
|---|---|---|
| FR | 2417299 | 9/1979 |
| FR | 0223580 | 5/1987 |
| WO | 02087664 | 11/2002 |
| WO | 2008110024 | 9/2008 |

* cited by examiner

*Primary Examiner* — Quynh-Nhu H Vu
(74) *Attorney, Agent, or Firm* — Sturm & Fix LLP (57) ABSTRACT

A disposable cassette intended for a metering pump for infusion consisting of just two components, namely, a hollow first component (1) forming a pump body, and a second component (5) collaborating with the hollow first component (1) to form a pumping zone (6) and comprising a flexible part (10) characterized in that the second component (5) further comprises a rigid part (9) secured to the flexible part (10) and able to be assembled with the hollow first component (1). The invention also relates to a method for manufacturing such a disposable cassette.

16 Claims, 9 Drawing Sheets

DISPOSABLE CASSETTE FOR AN INFUSION PUMP FOR MEDICAL USE AND METHOD FOR MANUFACTURE THEREOF

CROSS-REFERENCE TO RELATED APPLICATIONS

This application is a National Stage application of PCT/CH2010/000317 filed Dec. 20, 2010, claiming priority of CH 1983/09 filed Dec. 23, 2009, which are incorporated by reference herein in their entirety.

BACKGROUND OF THE INVENTION

1. Field of the Invention

The invention relates to a disposable cassette intended for a metering pump for infusion and to the method of manufacturing it.

Low-cost single-use gravity-fed infusion lines are known. These are commonly used in hospitals for irrigation (with saline) or for injecting various sensitive drugs. The flow rate is estimated by counting drops in a drip chamber and is regulated by a slide clamp. Neither the stability nor the precision are sufficient for certain applications. What is more, the absence of any electronics means that the suitability of the drug treatment - quantity - timing - patient cannot be monitored and checked. However, gravity-fed infusion has the advantage of being very cost-effective.

Electronic diaphragm or peristaltic pumps and gravity-fed flow controllers are also known. This equipment and its single use are expensive.

Also available on the market are disposable cassettes for infusion. Such cassettes are described in particular in the international application published under the number WO 02/087664. The appended FIGS. 1, 2a, 2b and 3 correspond respectively to FIGS. 2, 7a, 7b and 12 of this international application. These disposable cassettes comprise at least three components, namely:
- a hollow first component (a) forming a pump body, having an inlet (b) for the connection of an inlet tube and an outlet (c) for the connection of an outlet tube;
- a second component (d) collaborating with the hollow first component (a) to form a pumping zone (e) and comprising a flexible part (f) having a diaphragm-forming zone (g) carrying an inlet valve (h), an inlet lug (l), an outlet lug (m) bearing an outlet valve (i) and a peripheral rib (k) extending around the periphery of the diaphragm-forming zone (g) and around the periphery of the inlet (l) and outlet (m) lugs; and
- a rigid third component (j) which is distinct from the second component (d) and fits onto the hollow first component (a) with a view, in particular, to keeping the second component (d) in the hollow first component (a).

Figure 2A:
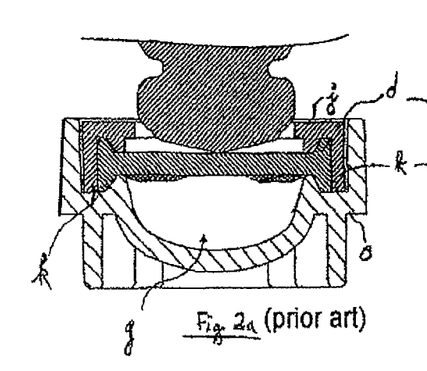
FIGS. 2a and 2b: views in cross section of the cassette of FIG. 1, illustrating its operation.
Figure 2B:
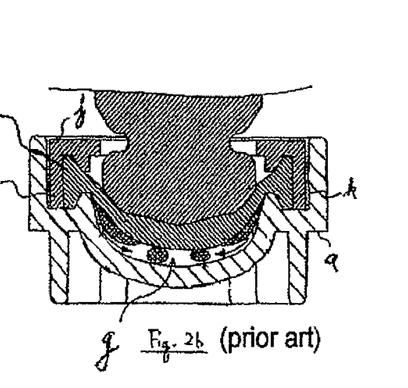

These cassettes have, in particular, the following disadvantages:
- when they are being used, the precision of the flow rate is insufficient, especially if the volume in each cycle is very small (of the order of 10 microlitres) because the diaphragm cannot be attached to the pump body repeatably enough across all of the manufactured batches;
- sealing is not reliable because it is achieved by trapping the peripheral rib (k) of the second component (d) between the hollow first component (a) and the third component (j), as can be seen in the attached FIGS. 2a and 2b,
- assembling the components that make up these cassettes presents problems of repeatability and therefore of retention of the diaphragm; and
- these components have complex shapes and are therefore more difficult and more expensive to manufacture.

It is an object of the invention to propose a disposable cassette for medical use which is simple, reliable, made up of a minimum number of component parts which are themselves easy to manufacture and to assemble. Because this cassette is disposable, its cost of manufacture has to be low and it needs to leave the smallest possible ecological footprint.

BRIEF DESCRIPTION OF THE INVENTION

According to the invention, the aforementioned object is achieved by means of a cassette for single use in an infusion pump which consists of just two components that are easy to produce on an industrial scale and to assemble.

The essential features of the cassette according to the invention are listed in item 1 below:
1. Cassette for single use in an infusion pump, consisting of:
   - a hollow first component forming a pump body, having an inlet orifice for the connection of an inlet tube and an outlet orifice for the connection of an outlet tube; and
   - a second component collaborating with the hollow first component to form a pumping zone and comprising a flexible part having:
     - a diaphragm-forming zone,
     - an inlet lug,
     - an inlet valve,
     - an outlet lug,
     - an outlet valve and
     - a peripheral rib extending around the periphery of the diaphragm-forming zone and around the periphery of the inlet and outlet lugs;
   this cassette being characterized in that the second component further comprises a rigid part secured to the flexible part and able to be assembled with the hollow first component.

Thus, by virtue of the special configuration of the cassette according to the invention, the diaphragm is anchored firmly, precisely and repeatably in the second component, which it is not in the cassettes according to WO 02/087664. The volume metered out during each operating cycle of the diaphragm is therefore highly repeatable across all the manufactured batches and is so at a very low production cost.

The cassette according to the invention therefore has the advantage of offering, for a cost similar to that of gravity infusion, the advantages of the precision of a diaphragm-type metering pump driven by an electronic controller comprising, for example, an electromagnet.

Additional advantageous features of the cassette according to the invention defined in item 1 above are itemized in items 2 to 15 below:
2. Cassette according to item 1, in which the second component is a component produced by two-shot injection moulding.
3. Cassette according to one of items 1 or 2, in which each of the inlet and outlet valves is separated from the diaphragm-forming zone by a surface.
4. Cassette according to one of items 1 to 3, in which the flexible part of the second component comprises a cavity.
5. Cassette according to one of items 1 to 4, in which the flexible part of the second component comprises:
   - an upper portion comprising the diaphragm-forming zone;
   - an annular portion;
   - a connecting portion connecting the disc-shaped portion and the annular portion;
   and in which the inlet and outlet lugs extend the annular portion on each side.

6. Cassette according to item 5, in which the inlet valve is born by the inlet lug and the outlet valve is born by the annular portion.
7. Cassette according to item 6, in which the upper portion is in the shape of a disc or annulus, the diameter of which is greater than that of the connecting portion.
8. Cassette according to one of items 1 to 7, in which at least one of the valves is in the form of a plate projecting from the lug that carries it, away from the diaphragm-forming zone.
9. Cassette according to one of items 1 to 8, in which the hollow first component has a hollow with a flat bottom equipped with housings to accommodate the valves.
10. Cassette according to item 9, in which the width of the valves is substantially equal or smaller than the width of the housings and the depth of the valves is substantially equal to the depth of the housings.
11. Cassette according to item 9 or 10, in which the housings each have a semi-frustoconical wall against which the corresponding valve is intended to come into contact under preload.
12. Cassette according to one of items 1 to 11, in which the hollow first component comprises at least one semi-circular groove, at least one valve of the second component has a rounded free end, the diameter of the semi-circular groove being smaller, when the hollow first component and second component have not been assembled, than the width $d_a$ of the rounded portion of the valve.
13. Cassette according to one of items 1 to 12, in which a concave region, intended to accommodate the material displaced when the peripheral rib is compressed, is formed in the flexible part at certain points adjacent to this peripheral rib.
14. Cassette according to one of items 1 to 13, in which the rigid part of the second component comprises at least one guide stud for the assembly with the hollow first component, which hollow first component comprises at least one hole to house the guide stud.
15. Cassette for single use in an infusion pump according to one of items 1 to 14, in which the hollow first component is made of plastic and, in the second component, the rigid part is made of polycarbonate and the flexible part is made of silicone.

It is of course possible to combine at least two of these items with one another, except where doing so is technically impossible.

Moreover, the invention also relates to a method of manufacturing the cassette according to the invention, the essentials of which are summarized in item 16 below:
16. Method of manufacturing a cassette according to one of items 1 to 15, in which:
   a hollow first component is manufactured and forms a pump body, having an inlet orifice for the connection of an inlet tube and an outlet orifice for the connection of an outlet tube;
this method being characterized in that it further comprises the following steps:
   a rigid part that can be assembled with the hollow first component is manufactured;
   a flexible part having:
      a diaphragm-forming zone,
      an inlet lug,
      an inlet valve,
      an outlet lug,
      an outlet valve,
      a peripheral rib extending around the periphery of the diaphragm-forming zone and around the periphery of the inlet and outlet lugs
   is secured to the rigid part;
   the hollow first component and the second component obtained by securing the rigid and flexible parts together are assembled.

This method therefore allows simple and rapid assembly of the components, for example by mounting or fitting the second component in the hollow first component. Assembly such as this is therefore repeatable and precise and in particular solves the problem of the "T" trapping of the peripheral rib (k) of the second component (d) that can be seen in the attached FIGS. 2a and 2b.

Items 17 to 20 below, which may be combined, provide additional advantageous features of the method according to the invention:
17. Method according to item 16, in which the flexible part is secured to the rigid part by overmoulding the flexible part in/on the rigid part using two-shot injection moulding.
18. Method according to item 16 or 17, in which the rigid part has a recess and the flexible part is injected into this recess.
19. Method according to one of items 16 to 18, in which the hollow first component and the second component are assembled by fitting the second component into the hollow first component.
20. Method according to one of items 16 to 19, in which the hollow first component and the second component further comprise at least one of the features defined in one of items 3 to 15.

BRIEF DESCRIPTION OF THE DRAWINGS

Other features and advantages of the invention will now be described in detail in the description which follows and which is given with reference to the attached figures which represent schematically:

FIG. 1: a cassette according to the prior art (cf. FIG. 2 of WO 02/087664) comprising at least three components;

DETAILED DESCRIPTION OF THE INVENTION

Cassette According to the Invention

The attached figures depict exemplary embodiments of the cassette according to the invention.

Figures 4, 5:
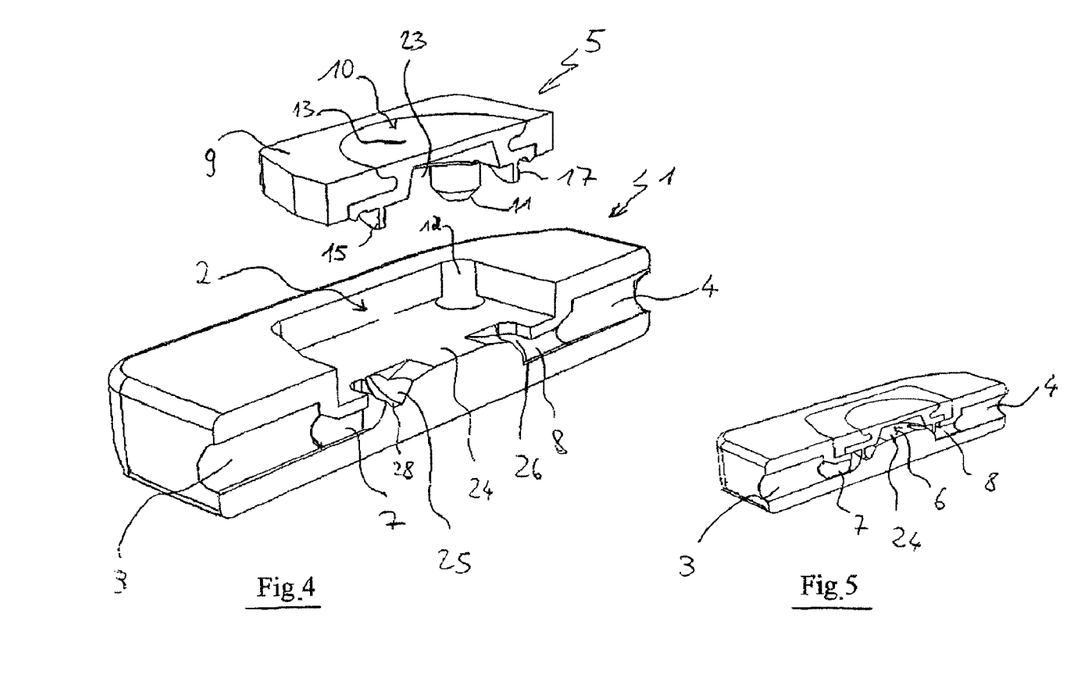
FIG. 4: a perspective view of the cassette according to the invention, prior to assembly.
FIG. 5: a perspective view of the cassette of FIG. 4, after assembly.
Figure 6:
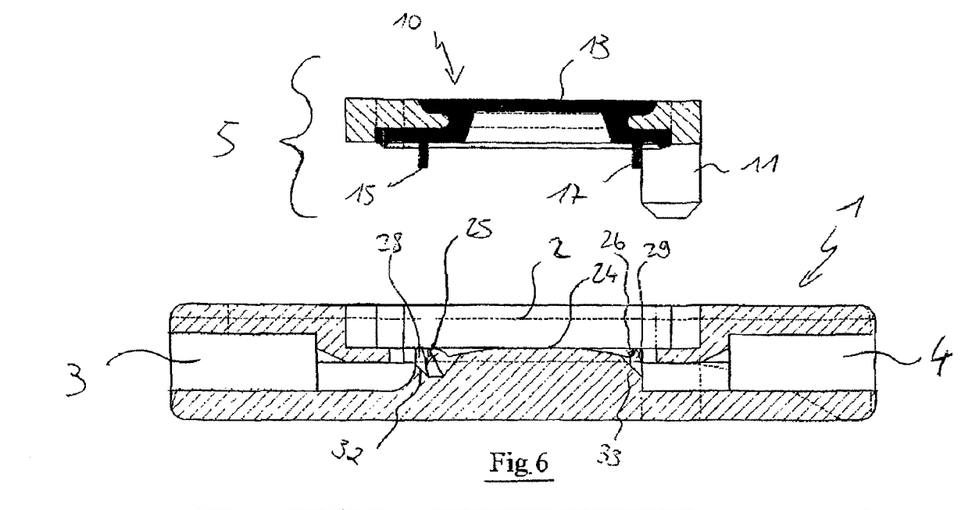
FIG. 6: a sectioned front view corresponding to FIG. 4.
Figure 7:
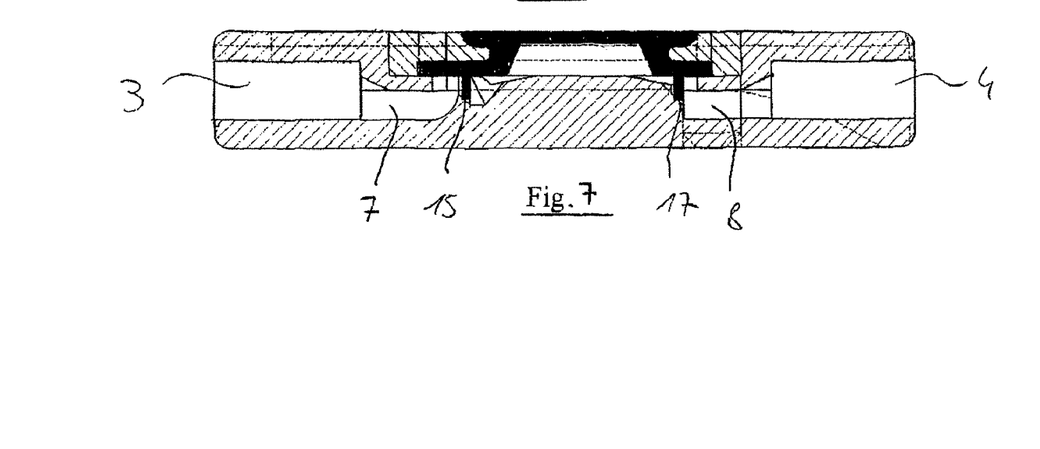
FIG. 7: a sectioned front view corresponding to FIG. 5.
Figure 8:
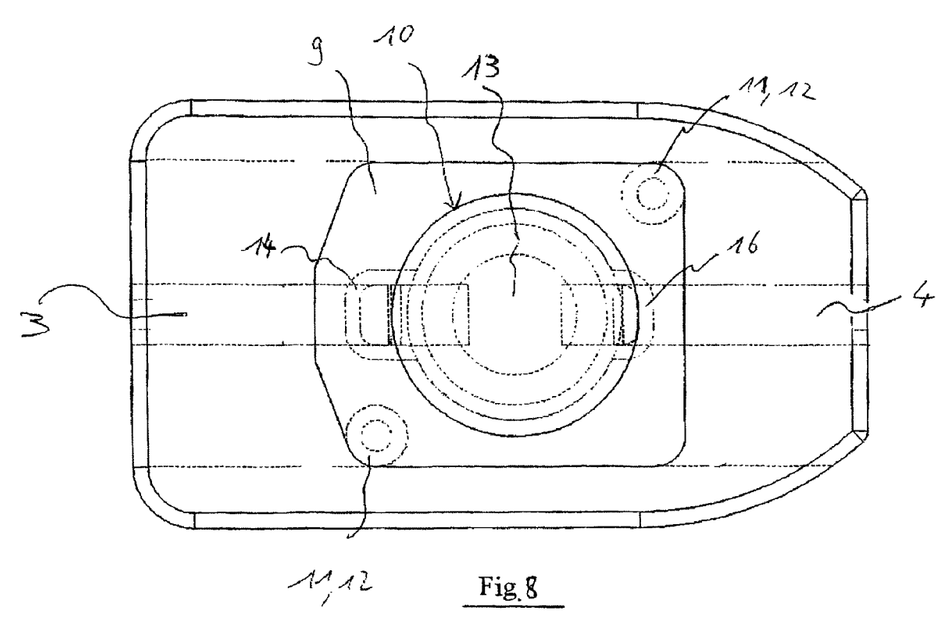
FIG. 8: a view from above corresponding to FIGS. 5 and 7.

As may be seen particularly from FIG. 4, the cassette according to the invention consists of just two components.

The first of these components, denoted overall by the reference numeral 1, comprises a hollow 2 intended in general to accommodate all of the second of these components, which is denoted by the reference numeral 5.

The hollow component 1 also comprises an inlet orifice 3 and an outlet orifice 4, the size of which is suited to accepting the tubes customarily used for infusions.

As can best be seen in FIG. 5, the inlet 3 and outlet 4 are provided on opposite sides of a pumping zone 6 with which they communicate via, respectively, an inlet lock 7 and an outlet lock 8.

The pumping zone 6 is the central space formed by assembling, here by fitting one inside the other, the second component 5 in the hollow first component 1.

The second component 5 consists of two parts secured to one another. This means that these two parts are not detachable under normal conditions of use of the cassette according to the invention. Put differently, it is as if these two parts were just one.

One of the parts is known as the "rigid part 9" and its role is essentially, firstly, to fit into the hollow 2 of the hollow first component 1 and, secondly, to support or hold the second part which is known as the "flexible part 10".

The respective dimensions of the rigid part 9 and of the hollow first component 1 are generally designed so that, once assembled one inside the other, there is neither any vertical clearance nor any horizontal clearance between them.

To make this assembly easier, the rigid part 9 preferably comprises at least one guide stud 11 and the hollow first component 1 comprises at least one hole 12 designed to house the guide stud 11. These guide studs 11 and corresponding holes 12 allow the second component 5 to be positioned in the hollow first component 1 with great precision.

Provided in the rigid part 9, more or less in the middle, is a central recess into which the flexible part 10, the shapes of which are best visible in FIGS. 9 to 12, sits.

Thus, the flexible part 10 has:
- a diaphragm-forming zone 13,
- an inlet lug 14,
- an inlet valve 15,
- an outlet lug 16,
- an valve 17 and
- a peripheral rib 18 extending around the periphery of the diaphragm-forming zone 13 and around the periphery of the inlet 14 and outlet 16 lugs.

The inlet 14 and outlet 16 lugs lie on opposite sides of the diaphragm-forming zone 13.

Figure 1:
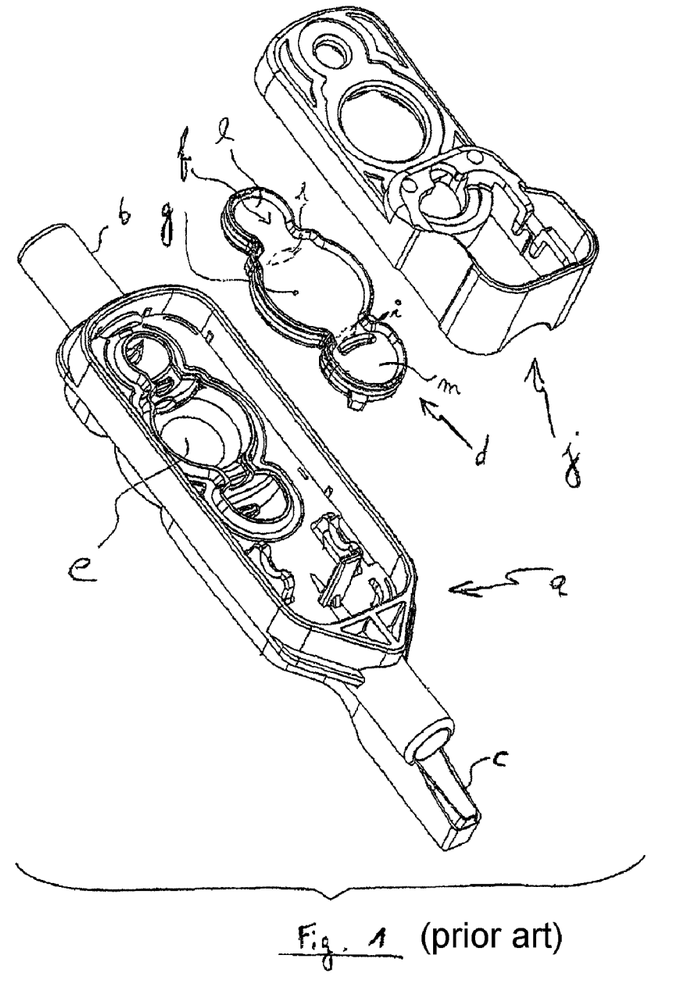

Unlike the diaphragm (d) of the prior art visible in FIG. 1, in which the inlet valve (h) lies on the diaphragm-forming zone, that is, in the pumping zone (e), according to the invention, the inlet valve 15 is preferably connected to the inlet lug 14.

This means that it is possible to provide, between the valves 15 and 17 and the diaphragm-forming zone 13, a surface 19 and a surface 20 respectively. These surfaces 19, 20, which preferably lie on the peripheral rib 18, are intended to rest against the hollow first component 1 at the time of the assembly.

Figure 9:
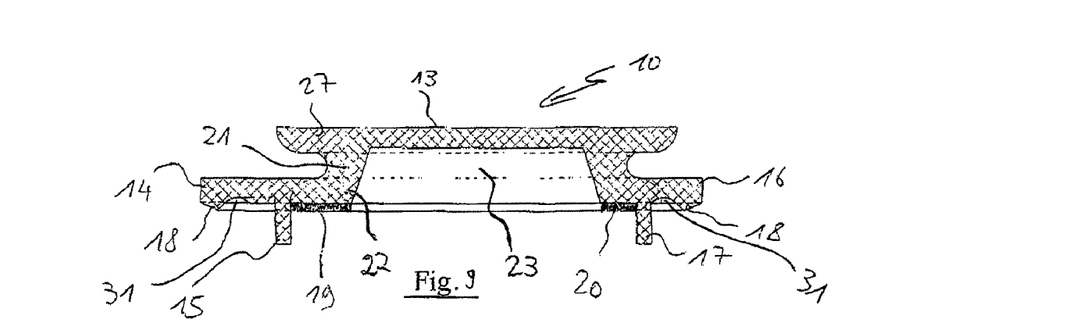
FIG. 9: a sectioned front view of the flexible part of the second component.

The inlet 15 and outlet 17 valves may have the form of a plate and project substantially at right angles from the lugs 14, 16 which carry them, extending downwards in FIG. 9, that is to say away from the diaphragm-forming zone 13.

Figure 10:
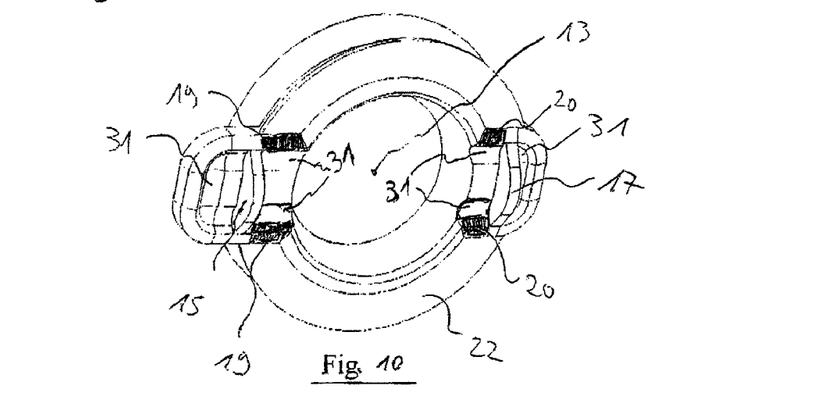
FIG. 10: a view from underneath corresponding to FIG. 9.

As can be seen particularly from FIGS. 9 and 10, the flexible part 10 may comprise an upper portion 27, for example in the shape of a disc, of which the diaphragm-forming zone 13 forms part, a substantially cylindrical or frustoconical connecting portion 21 which separates the diaphragm-forming zone 13 and raises it from an annular portion 22 which is extended on each side by the lugs 14, 16.

Figure 3:
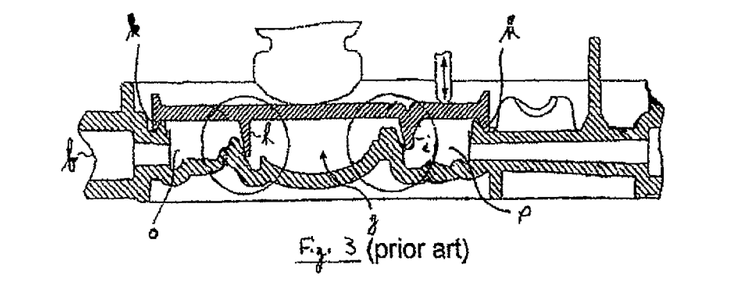
FIG. 3: a view in longitudinal section of the cassette according to FIGS. 1, 2a and 2b.

Unlike the diaphragm (d) of the prior art visible in FIG. 3, in which the outlet valve (i) lies on the lug (f), that is, in the fluid outlet zone (p), according to the invention, the outlet valve 17 is preferably connected to the annular portion 22.

Thanks to the raising formed by the connection portion 21, there is a cavity 23 in the flexible part 10.

It is preferable to ensure that the disc-shaped portion 27 has a diameter greater than that of the connecting portion 21, so as to increase the area for contact between the flexible part 10 and the rigid part 9. Specifically, increasing this contact area makes it possible to improve the connection or bond between these parts 9 and 10 and therefore improve the degree to which they are inseparable.

As may be seen by referring once again to FIG. 4, when the flexible part 10 and the hollow first component 1 are assembled, a pumping zone 6 is created between the bottom 24 (cf. FIGS. 4 and 5) of the hollow 2 of the hollow first component 1 and the diaphragm-forming zone 13.

For preference, this bottom 24 is flat and has housings 25 and 26 to accommodate the valves 15 and 17 respectively. It therefore also allows the peripheral rib 18 to be fully compressed against the hollow first component 1 after assembly. Thus, the peripheral rib 18 acts as a seal and as a sterile and non-pyrogenic barrier against the outside and also against the (laser or ultrasonic) welding which may potentially generate microdrops of plastic or of fumes which when infused into the blood system are pyrogenic.

Thanks to the designs of the hollow first component 1 and of the flexible part 10, when the cassette according to the invention is used, when the diaphragm-forming zone 13 is depressed to lower it, the pressure in the pumping chamber increases, allowing the outlet valve 17 to open by flexing. Conversely, when the diaphragm-forming zone 13 rises back up again, the pressure in the pumping zone 6 decreases and allows the inlet valve 15 to open by flexing.

Thus, the valves 15, 17 do not perform any downwards movement, that is to say that there is no friction between these valves and the hollow first component 1 and therefore no wearing of the valves 15, 17. The situation therefore differs from that of the aforementioned prior art in which the inlet (h) and outlet (i) valves rub against the hollow first component each time the diaphragm rises and falls respectively.

This problem of friction is of particular importance because these components are intended to undergo up to several million diaphragm movements and therefore appreciable valve wear which results in losses of flow rate and risks to the health of the patient.

Also, as may be seen in FIGS. 4 and 5, the valve 15 moves into the small space of the housing 25 during the fluid suction phase into the pumping zone 23.

Similarly, the valve 17 moves into the small zone of the housing 26 during the fluid discharge towards the outlet.

Such features contribute to the obtention of an extremely accurate control of the flow.

Figure 11:
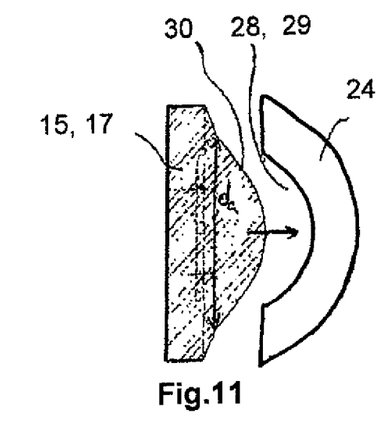
FIGS. 11 and 12: side views, before and after assembly respectively, of a valve of the flexible part.
Figure 12:
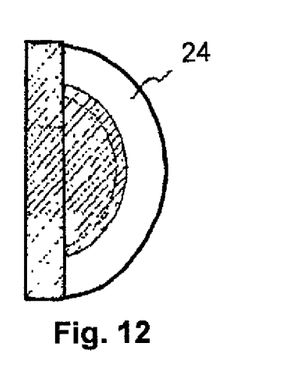
Figure 13:
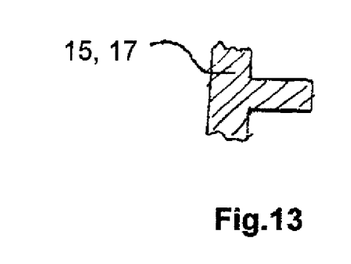
FIGS. 13 and 14: details of the valves, before and after assembly respectively.
Figure 14:
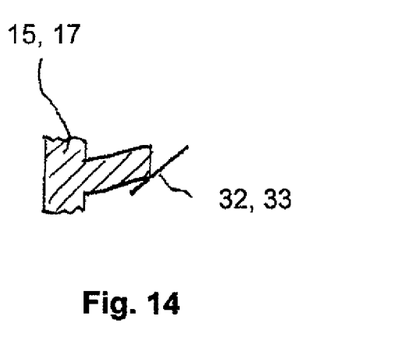

Preferably, as may be seen in FIGS. 11 and 12, the valves 15, 17 have, at their free end, a rounded shape 30, and the flat bottom 24 of the hollow first component 1 has semi-circular grooves 28, 29 designed to accommodate the valves 15, 17.

However, as may be seen by examining FIGS. 11 and 12 in turn, these respectively depicting the non-assembled state and the assembled state, the diameters of the semi-circular grooves are designed to be smaller than the width $d_a$ of the rounded portions 30 of the valves 15, 17. What this means is that, at the time of assembly, these valves are trapped along their sides, affording better sealing.

Figure 15:
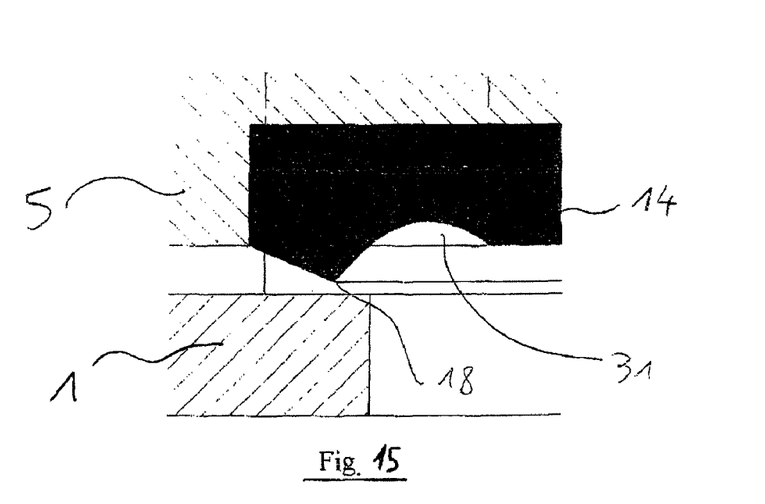
FIGS. 15 and 16: details of the peripheral rib of the flexible part of the second component, before and after assembly respectively.
Figure 16:
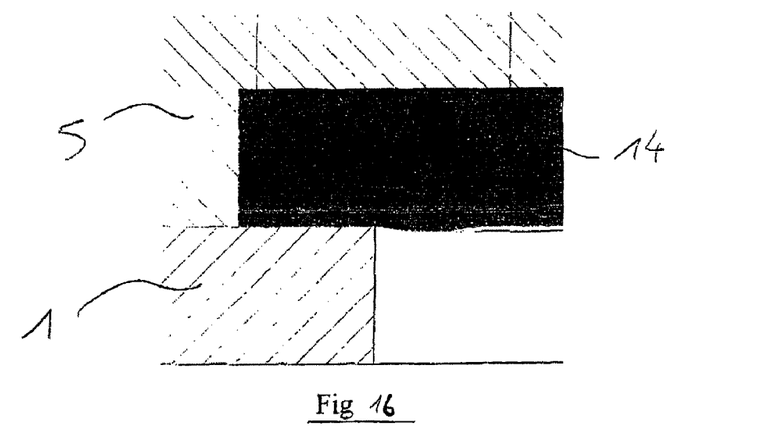

FIGS. 15 and 16 show an alternative form for the peripheral rib 18 of the annular portion 21. This rib has a substantially triangular cross section and concave regions 31 are provided beside it, at certain points on the flexible part 10, particularly on the lugs 14, 16. These concave regions 31 are intended to accommodate the material displaced when the rib 18 is compressed. This then yields better sealing at the time of assembly of the hollow first component 1 and of the second component 5 and achieves compliance with the "GMD" (Good Microorganism Design) standard.

As previously explained, the width (or diameter of the semi-circular grooves) of the valves 15,17 is preferably substantially equal or smaller than the width of the housings 25 and 26. Also, as may be seen in particular in FIGS. 4 to 7, the depth of the housings 25 and 26 is preferably substantially equal to the depth (or length towards the bottom) of the valves 15,17.

This particularly appears when comparing FIG. 3 with FIG. 4. It results from such a comparison that the cassette according to the invention, because of the small size of the housings 25 and 26, does not form any fluid inlet and outlet dead zones, as those which are designated by (o) and (p) in the cassette of the prior art represented in FIG. 3 and which are relatively large. In the cassette of the invention the absence of dead zones between the inlet 7 and outlet 8 locks and the respective valves 15 and 17 has the advantage of greatly reducing the risks of recirculation or stagnation of substances, something which would present a danger to the patient, and to avoid the presence of air bubbles, because the latter are expelled during the initiation phase.

According to another advantageous alternative form visible in FIGS. 6, 7, 13 and 14, the housings 25, 26 of the flat bottom 24 have, on the upstream side, respective walls 32, 33 that are inclined in the direction of flow of the fluid (from left to right in the figures). Thus, following assembly (FIG. 14), the upstream faces of the valves 15, 17 are in preloaded contact with the semi-frustoconical walls 32, 33, and this further improves the precision of the cassette according to the invention.

Figures 17, 18:
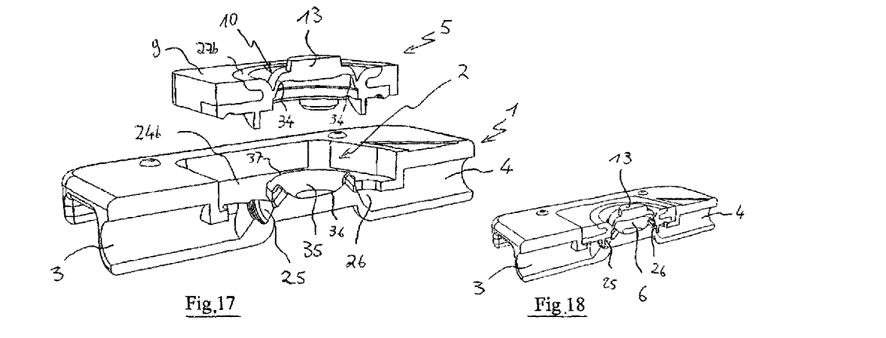
FIGS. 17 and 18: an advantageous alternative form of the cassette according to the invention.

According to an advantageous alternative form of embodiment of the cassette according to the invention depicted in FIGS. 17 and 18, the upper portion 27*b* of the flexible part 10 is not in the shape of a disc but has an annular shape. The diaphragm-forming zone 13 is connected to the connecting portion 21 by a deformable portion 34.

The flat bottom 24*b* of the hollow 2 of the hollow first component 1 has, in addition to the housings 25 and 26, a bowl 35 formed both by an indentation 36 and by a circular rim 37 that is raised above the flat bottom 24*b*.

The pumping zone 6 formed here by the diaphragm-forming zone 13 and the bowl 35 communicates, as in the previous embodiment, with the inlet 3 and outlet 4 orifices via the housings 25 and 26.

The upper portion 27*b*, the deformable portion 34 and the diaphragm-forming zone 13 of this advantageous alternative form are described in detail in the international patent application filed on the same day as this patent application, by the same applicant and under the title "Metering pump device for medical use" and the content of which is incorporated by reference into this patent application.

Method According to the Invention

The cassette according to the invention may be produced by implementing a method in which:

- the hollow first component 1 is manufactured;
- a rigid component 9 is manufactured, this being intended to become the rigid part 9 of the second component 5 and which is able to be assembled with the hollow first component 1;
- a flexible component 10 intended to become the flexible part 10 of the second component 5 is secured to the rigid component 9;
- the hollow first component 1 and the second component 5 obtained by securing the rigid 9 and flexible 10 parts together are assembled.

The type of assembly between the hollow first component 1 and the second component 5 depends on the shape and the way in which they are intended to collaborate. It may, in particular, be a mounting or a fitting of the second component 5 in the hollow first component 1.

It is particularly advantageous to secure the flexible part 10 to the rigid part 9 by overmoulding the flexible part 10 in/on the rigid part 9 by two-shot injection moulding.

What is meant here by "two-shot injection moulding" is sequential injection of the two materials that form the rigid part and the flexible part, that is to say an injection that takes place in two steps, this English term "two-shot injection moulding" being fairly widely recognized.

According to an advantageous alternative form of the method according to the invention, the rigid part 9 has a central recess and the flexible part is produced by injecting material into this recess.

Two-shot injection moulding is a technique particularly well suited to the invention because, on the one hand, it allows components with a certain level of complexity such as the flexible part 10 to be created easily and, on the other hand, two-shot injection moulded components behave as a single component, that is to say that once joined together the component parts thereof are inseparable under normal conditions of use of the cassette. Thus, the rigid part 9 supports the flexible part 10 very precisely and repeatably. This is of great importance because, when the cassette is being used, the precision of the flow rate is directly proportional to the precision of the volume displaced in each pumping cycle.

In addition, two-shot injection moulding makes it possible to create a second component 5 that is very small, with minimal thicknesses of material. That makes it possible to shorten the time taken for the silicone (or other material of which the flexible part 10 is made) to vulcanize, and therefore the pump manufacturing cycle time.

Finally, the connection between the rigid part and the flexible part is perfectly sealed when these parts have been joined together by two-shot injection moulding.

Of course, the moulds used for two-shot injection moulding have all the shapes necessary to obtain the desired configuration for the flexible part 10 (lugs 14, 16; valves 15, 17; cavity 23; flat bottom 24 or 24*b*; housings 25, 26, etc.).

Once the second component 5 has been fitted into the hollow first component 1, the connection between these components can be made fluidtight in respect both of liquids and gases.

This can be achieved by any appropriate means, particularly by bonding or welding. For preference, use is made of ultrasonic or laser welding.

Materials

The material of which the hollow first component is made is of little importance. However, it will be a plastic chosen so that it can be welded or bonded to the rigid part. The latter is preferably made of polycarbonate.

The flexible part may be made of an elastomer such as EPDM or a polyurethane, or, for preference, may be made of silicone. The duration of the manufacturing cycle to manufacture a cassette according to the invention comprising a flexible part made of silicone is far longer than for injecting some other plastic because of the time taken for the silicone to vulcanize. This duration is also dependent on the mass and thicknesses of silicone. Nonetheless, in the cassette according to the invention, the flexible part of the second component has the advantageous special feature of being far smaller than the hollow first component. It then follows that the thicknesses and volumes of silicone are small and the manufacturing time remains short.

Uses

Volumetric Metering Pump

Before the cassette according to the invention is used, a fluid inlet tube is introduced in the known way into the inlet orifice 3 and a fluid outlet tube is introduced into the outlet orifice 4. The tubes are generally held in the orifices by bonding.

Next, the disposable cassette according to the invention is slid onto a controller which, for example, consists of an electromagnet or of an electromagnetic actuator, of command and control electronics, and possibly of a screen. Such an electromagnet is described for example in the international application published under the number WO 2008/110024.

The disposable cassette according to the invention may advantageously be actuated by the driving part of the reciprocating positive-displacement diaphragm pump described in detail in the international patent application filed on the same day as the present patent application, by the same applicant, under the title "Reciprocating positive-displacement diaphragm pump for medical use" and the content of which is incorporated by reference into this patent application.

Thus, the cassette according to the invention offers the following advantages:

a very rigid and stable adhesion between the flexible and rigid parts of the second component;

said adhesion is very independent on the necessary tightness between both parts;

the diaphragm does not rely on the motor housing other than the piston and when in position, it does not touch the bottom of the first hollow component;

the configuration of the cassette allows the obtention of a very high precision, which is surprising when using flexible silicone;

the cassette has a compacity which allows a good relative precision of its dimensions;

the 0.1 to 100 µl volumes and the flows which are obtained with the selected impulse durations, allow liquid speeds in the cavity which expel the air bubbles and remove in a few cycles the bubbles blocked in the cavity. These speeds are about one meter/second. They are largely sufficient to quickly evacuate the residual air bubbles from the pumping chamber. This is surprising for those skilled in the art who know this technology; and the cassette has the capacity of rapidly initiating by expelling the air bubbles, which allows to avoid the flow errors, even when the liquid source is located below the pump.

In addition, by virtue of the small number of component parts thereof and its ease of manufacture, the cassette according to the invention has a smaller ecological footprint than that of the cassettes of the prior art.

The invention claimed is:

1. Cassette for single use in an infusion pump, comprising:
a hollow first component forming a pump body, having an inlet orifice and an inlet lock for the connection of an inlet tube and an outlet orifice and an outlet lock for the connection of an outlet tube; and
a second component collaborating with the hollow first component to form a pumping zone and comprising a flexible part having:
a diaphragm-forming zone,
an inlet lug,
an inlet valve,
an outlet lug,
an outlet valve and
a peripheral rib extending around the periphery of the diaphragm-forming zone and around the periphery of the inlet and outlet lugs; and
wherein the second component further comprises a rigid part secured to the flexible part and able to be assembled with the hollow first component,
wherein the diaphragm-forming zone, the inlet lug, the inlet valve, the outlet lug, the outlet valve and the peripheral rib form a single component,
wherein the bottom of the hollow of the first component comprises housings to receive said valves, said housings directly lead into said inlet and outlet locks, respectively, wherein the inlet valve is born by the inlet lug and the outlet valve is born by an annular portion and
wherein the peripheral rib comprises surfaces separating the inlet and the outlet valves; wherein the inlet and outlet valves are separated from the diaphragm-forming zone by a surface and resting against said hollow first component.

2. Cassette according to claim 1, in which the second component is a component produced by two-shot injection moulding.

3. Cassette according to claim 1, in which the flexible part of the second component comprises a cavity.

4. Cassette according to claim 1, in which the flexible part of the second component comprises:
an upper portion comprising the diaphragm-forming zone;
a connecting portion connecting the disc-shaped portion and the annular portion; and in which the inlet and outlet lugs extend the annular portion on each side.

5. Cassette according to claim 1, in which the upper portion is in the shape of a disc or annulus, wherein the shape of disc or annulus portion has a diameter greater than that of the connecting portion.

6. Cassette according to claim 1, in which at least one of the valves is in the form of a plate projecting from the lug that carries it, away from the diaphragm-forming zone.

7. Cassette according to claim 6, in which the width of the valves is substantially equal or smaller than the width of the housings and the depth of the valves is substantially equal to the depth of the housings.

8. Cassette according to claim 7, in which the housings each have a semi-frustoconical wall against which the corresponding valve is intended to come into contact under pre-load.

9. Cassette according to claim 1, in which the hollow first component comprises at least one semi-circular groove, at least one valve of the second component has a rounded free end, the diameter of the semi-circular groove being smaller, when the hollow first component and second component have not been assembled, than the width $d_a$ of the rounded portion of the valve.

10. Cassette according to claim 1, in which a concave region, intended to accommodate the material displaced when the peripheral rib is compressed, is formed in the flexible part at certain points adjacent to this peripheral rib.

11. Cassette according to claim 1, in which the rigid part of the second component comprises at least one guide stud for the fitting into the hollow first component, which hollow first component comprises at least one hole to house the guide stud.

12. Cassette for single use in an infusion pump according to claim 1, in which the hollow first component is made of plastic and, in the second component, the rigid part is made of polycarbonate and the flexible part is made of silicone.

13. Method of manufacturing a cassette comprising:
   a hollow first component is manufactured and forms a pump body, having an inlet orifice and an inlet lock for the connection of an inlet tube and an outlet orifice and an outlet lock for the connection of an outlet tube; wherein the bottom of the hollow of the hollow first component comprises housings to receive said valves, said housings directly lead into said inlet and outlet locks, respectively; wherein the method further comprises:
   a rigid part that can be assembled with the hollow first component is manufactured;
   a flexible part having:
      a diaphragm-forming zone,
      an inlet lug
         an inlet valve intended to be received in said housing,
      an outlet lug,
         an outlet valve intended to be received in said housing,
      a peripheral rib extending around the periphery of the diaphragm-forming zone and around the periphery of the inlet and outlet lugs is secured to the rigid part; wherein the diaphragm-forming zone, the inlet lug, the inlet valve, the outlet lug, the outlet valve and the peripheral rib form a single component, and wherein the inlet valve is born by the inlet lug and the outlet valve is born by an annular portion: the peripheral rib comprises surfaces separating the inlet and the outlet valves: wherein the inlet and outlet valves are separated from the diaphragm-forming zone by a surface and intended to rest against said hollow first component, and
   the hollow first component and the second component obtained by securing the rigid and flexible parts together are assembled.

14. Method according to claim 13, in which the flexible part is secured to the rigid part by overmoulding the flexible part in/on the rigid partusing two-shot injection moulding.

15. Method according to claim 13, in which the rigid part has a recess and the flexible part is injected into this recess.

16. Method according to claim 13, in which the hollow first component and the second component are assembled by fitting the second component into the hollow first component.

* * * * *